United States Patent [19]

Baker

[11] Patent Number: 5,630,507
[45] Date of Patent: May 20, 1997

[54] SINGLE-ACTION LATCH

[75] Inventor: Terry L. Baker, Indianapolis, Ind.

[73] Assignee: Carr Metal Products, Inc., Indianapolis, Ind.

[21] Appl. No.: 598,921

[22] Filed: Feb. 9, 1996

[51] Int. Cl.$^6$ ................................................. B65D 45/00
[52] U.S. Cl. ...................... 206/370; 206/1.5; 292/97; 292/DIG. 49
[58] Field of Search ........................... 292/247, 250, 292/113, 100, DIG. 49, 97, 99; 206/570, 571, 363, 370, 438, 1.5

[56] References Cited

U.S. PATENT DOCUMENTS

| | | |
|---|---|---|
| 2,744,778 | 5/1956 | Cooke . |
| 2,893,771 | 7/1959 | Claud-Mantle . |
| 3,338,387 | 8/1967 | Ferry ................................ 206/370 |
| 4,241,833 | 12/1980 | Luebcke .......................... 206/570 |
| 4,915,913 | 4/1990 | Williams et al. . |
| 5,257,839 | 11/1993 | Nielsen et al. . |

Primary Examiner—Jacob K. Ackun
Attorney, Agent, or Firm—Woodard, Emhardt, Naughton, Moriarty & McNett

[57] ABSTRACT

A single-action latch for use on a medical case which includes a storage tray and a closing lid includes a latch base with a mounting surface and rivet holes for attaching the latch base to the storage tray. A hook portion is pivotally attached to the latch base by means of a cylindrical pin. A release/closing lever is pivotally attached to the latch base by means of a cylindrical pin. A pair of oppositely-disposed connecting links is provided so as to interconnect the hook portion with the release/closing lever. The connecting links separate the hook portion from the latch base and the release/closing lever from the latch base. The latch is operable between a closed condition and an open condition and the lever is pivotally movable so as to transition the latch from the closed condition to the opened condition and then back to the closed condition. The positioning of the connecting links relative to the pivot axis of the lever ensures an over-the-center linkage arrangement so as to provide a positive snap-closed design.

17 Claims, 5 Drawing Sheets

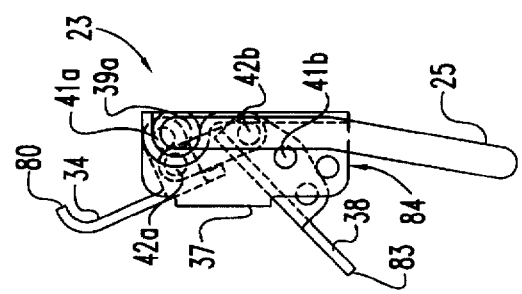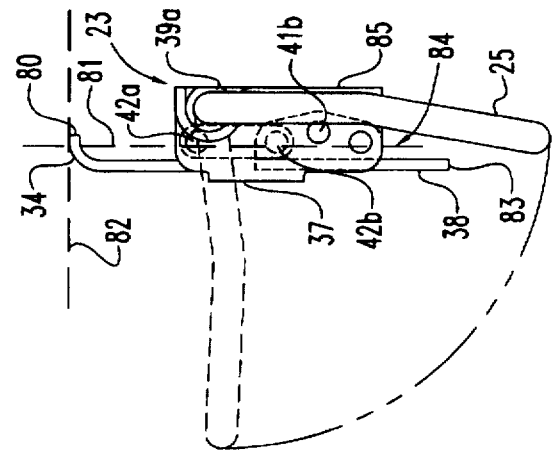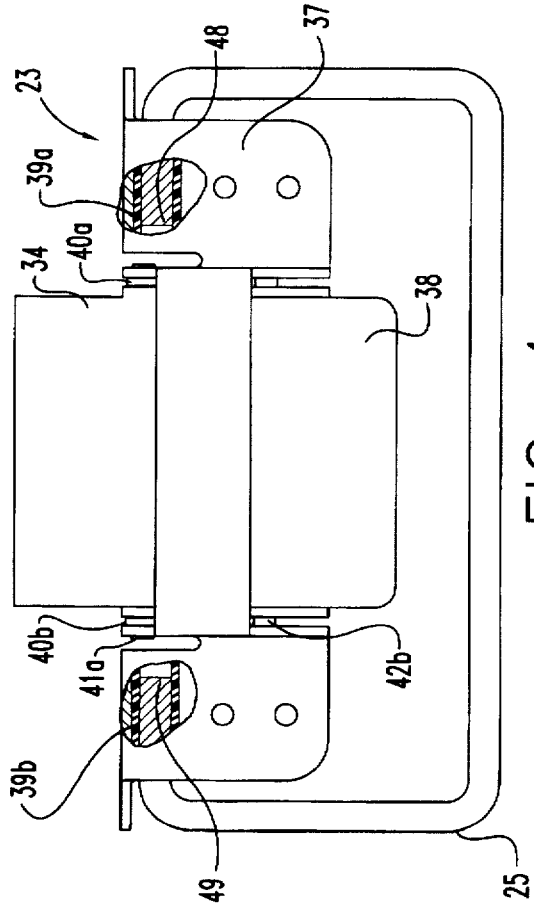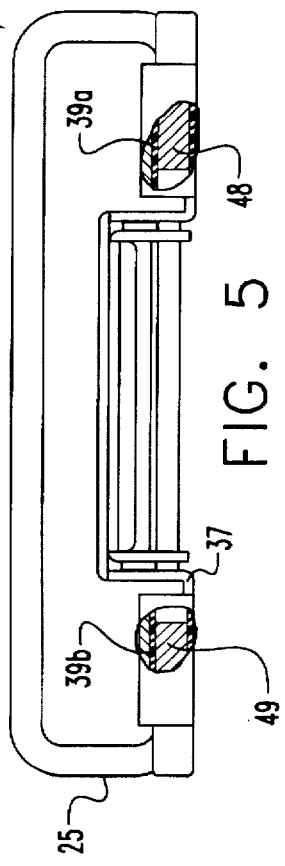

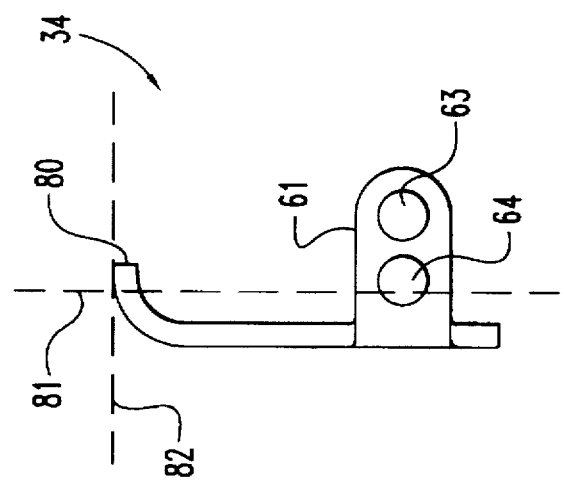
FIG. 13
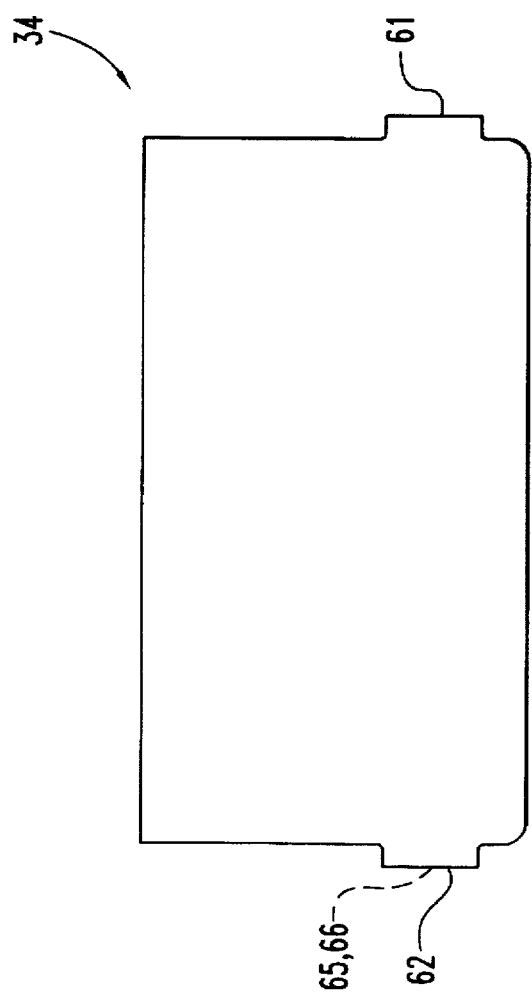
FIG. 11
FIG. 12
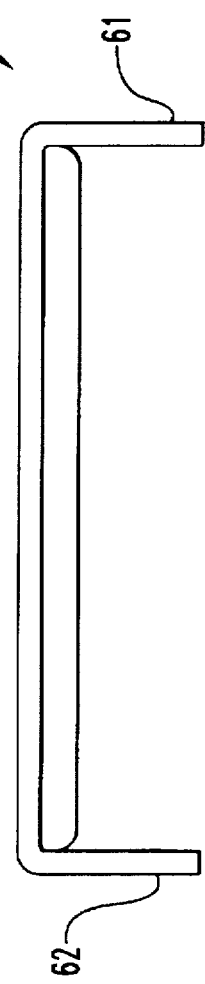

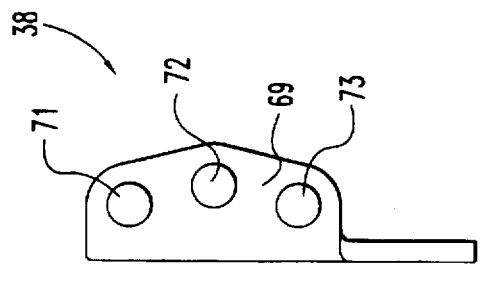
FIG. 16
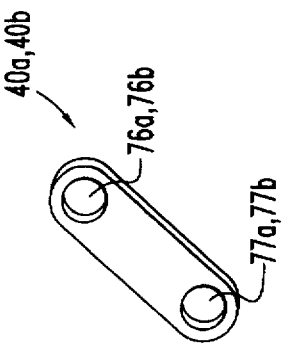
FIG. 17
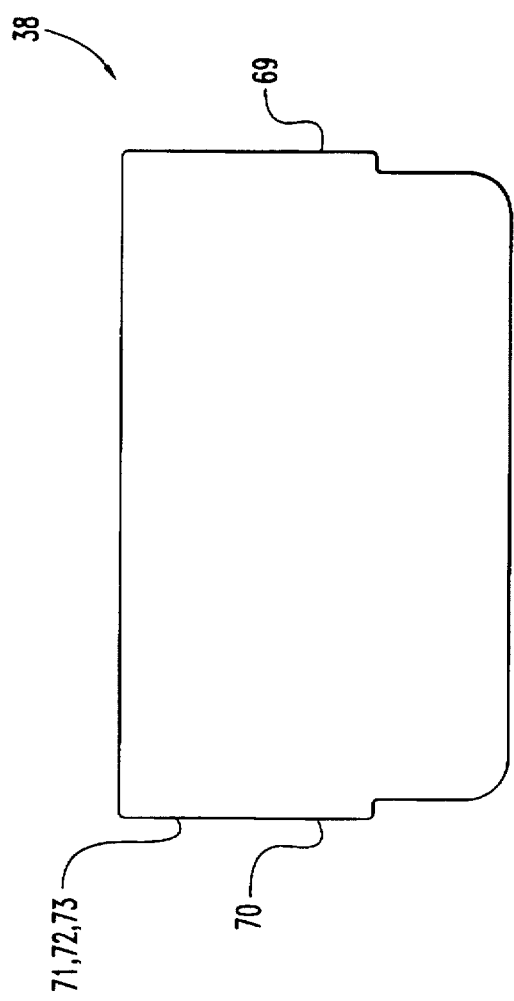
FIG. 14
FIG. 15
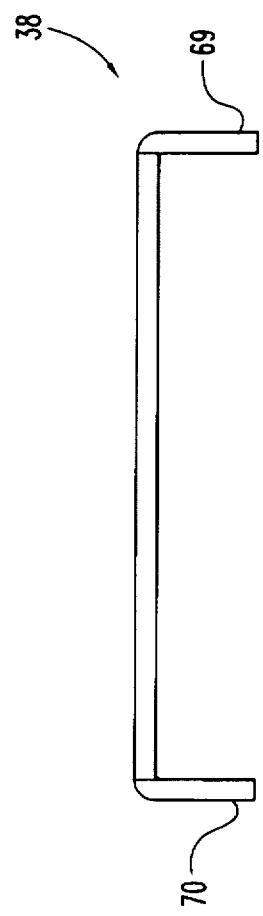

SINGLE-ACTION LATCH

BACKGROUND OF THE INVENTION

The present invention relates in general to latches for cases and containers where a lid member is secured to a tray portion by means of one latch or a plurality of latches. More specifically, the present invention relates to a single-action latch for a medical case where the latch can be opened and closed by the use of only one finger. Further, the opening and closing motion is continuous and singular in nature.

At the present time there are a variety of cases which are used for the storage and transport of equipment, instruments, and supplies and which include a tray portion and a closing lid member. While the lid member may be hinged along one edge to the tray portion, the lid member may also be separate and not attached to the tray portion. Regardless of the specific lid configuration, at least one side of the lid member must lift or pivot away from the tray portion in order for the end user to gain access to the interior storage area of the tray portion. Accordingly, it is desired to be able to secure this one side in a closed condition against a corresponding side or edge of the tray portion. When the lid is completely separate from the tray portion, a pair of latches, oppositely disposed, are normally used to secure the lid to the tray portion. A common means of securing the lid member and tray portion together is to use a multi-component latch with a particular operating linkage. Typically one portion of the latch is anchored to the outer wall of the tray portion and a cooperating clamp portion of the latch extends up and over the outer peripheral edge of the lid member. Through the arrangement and interaction of various linkage members, the clamp portion is able to assume a free state so that it can be oriented over the edge of the lid member and then moved into a locked orientation.

One example of what has been only generally described is provided by U.S. Pat. No. 4,915,913 which issued Apr. 10, 1993 to Williams et al. Another example is provided by U.S. Pat. No. 2,893,771 which issued Jul. 7, 1959 to Claude-Mantle.

When a latch is being designed for a medical case, there are certain considerations which need to be factored into the latch configuration. Some of these considerations include the aesthetics of the design, the size, acceptable materials, and the absence of sharp corners or edges. Other considerations should include the specific method of use, the relative ease or difficulty in opening and closing the medical case, how secure is the latch, and whether there are any loose or free moving components parts.

While different customers and end users may prioritize these various considerations differently, the method of use and the relative ease or difficulty in manipulating the latch are believed to be near the top of every list. When the latch is to be used for a medical case, it is important to have a latch which is free of sharp corners or edges which might cut or puncture surgical gloves. If dangling or freely moving component parts can be avoided, there will be less noise and less risk of something catching on the component part. In turn, this then reduces the risk of the case being jarred or spilled. While it is important to have a secure clamping action of the lid member onto the tray portion, it is equally important to be able to easily release the latch.

The present invention addresses each of these design considerations in a novel and unobvious way. The resultant latch according to a typical embodiment of the present invention has an aesthetically pleasing configuration, no sharp corners or edges, no freely moving or dangling components parts, and the overall configuration is easy to use and convenient. A unique linkage arrangement is provided which enables the latch to be closed by a single action which can be manipulated by one finger. In the closed condition, there is an over-the-center arrangement which provides a snap-lock feature. While the latch is very secure and reliably holds the lid member onto the tray portion due to this particular design, the latch can be manually released with a single action by the use of one finger. However, the over-the-center snap-lock feature prevents the latch from coming unhooked due simply to transport and handling movement and vibrations.

While single-action latch movement may have been employed in earlier latch designs, the specific style and configuration of the present invention is still believed to be novel an unobvious. For example, U.S. Pat. No. 2,744,778 which issued May 8, 1956 to Cooke, discloses a latch-type of device which seems to have a single-action manner of closing, based on the FIG. 4 illustration. However, as can be seen, this design is significantly different from the present invention and includes a number of the previously suggested disadvantages or drawbacks when designing a latch for a medical case.

SUMMARY OF THE INVENTION

A single-action latch for use on a container having a storage tray and closing lid according to one embodiment of the present invention comprises a latch base having a mounting surface and means for attaching the latch base to the storage tray, a hook portion pivotally attached to the latch base, a release/closing lever pivotally attached to the latch base and a pair of oppositely-disposed connecting links wherein each connecting link is connected at one end to the hook portion and at an opposite end to the lever such that the latch is operable between a closed condition wherein the hook portion secures tile closing lid to the storage tray and an open condition wherein the lid may be separated from the storage tray, the lever being pivotally movable so as to transition the latch from the closed condition to the open condition and back to the closed condition.

One object of the present invention is to provide an improved single-action latch for use on a container.

Related objects and advantages of the present invention will be apparent from the following description.

BRIEF DESCRIPTION OF THE DRAWINGS

FIG. 4 is a front elevational view of a latch which comprises a portion of the FIG. 1 medical case.

FIG. 5 is a top plan view of the FIG. 4 latch.

FIG. 6 is a side elevational view of the FIG. 4 latch in a closed condition.

FIG. 7 is a side elevational view of the FIG. 4 latch in an open condition.

FIG. 11 is a front elevational view of a hook comprising a portion of the FIG. 4 latch.

FIG. 12 is a top plan view of the FIG. 11 hook.

FIG. 13 is a side elevational view of the FIG. 11 hook.

FIG. 14 is a front elevational view of a lever comprising a portion of the FIG. 4 latch.

FIG. 15 is a top plan view of the FIG. 14 lever.

FIG. 16 is a side elevational view of the FIG. 14 lever.

FIG. 17 is a perspective view of one connecting link comprising a portion of the FIG. 4 latch.

DESCRIPTION OF THE PREFERRED EMBODIMENT

Figure 2A:
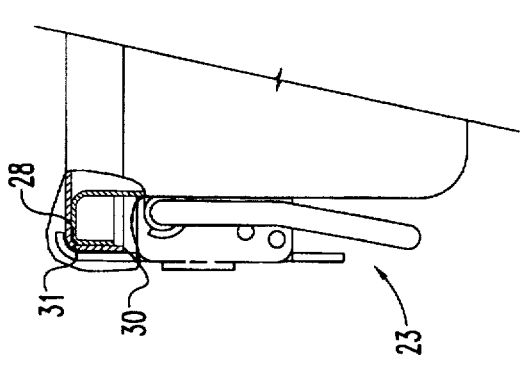
FIG. 2A is an enlarged corner detail of the FIG. 2 medical case.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 3:
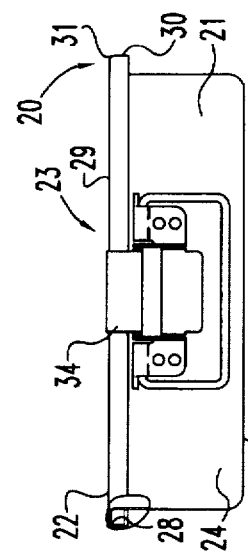
FIG. 3 is an end elevational view of the FIG. 1 medical case.
Figure 1:
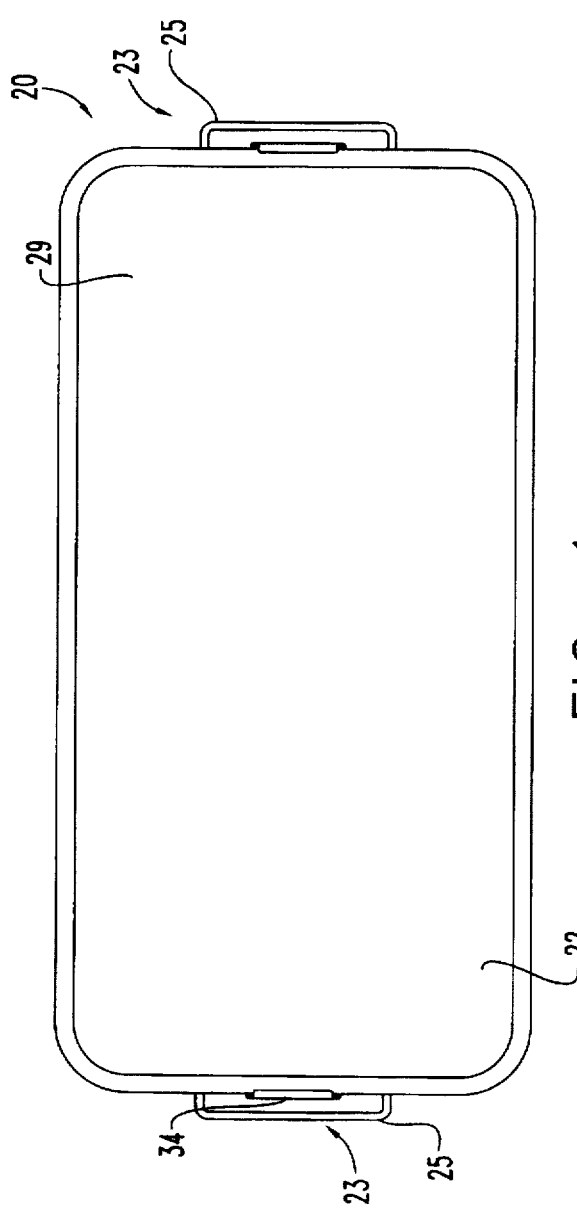
FIG. 1 is a top plan view of a medical case including a pair of oppositely disposed latches according to a typical embodiment of the present invention.
Figure 2:
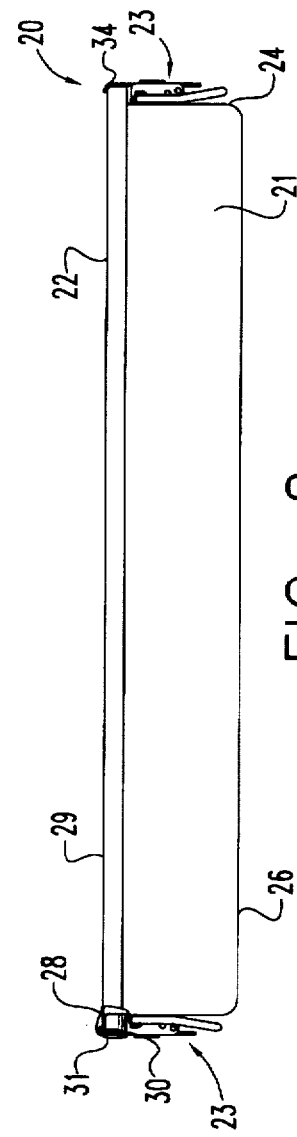
FIG. 2 is a side elevational view of the FIG. 1 medical case with the bail handles in a lowered position.

Referring to FIGS. 1-3, there is illustrated a medical case 20 which includes a tray portion 21 for storage, lid 22, and a cooperating pair of oppositely disposed latches 23 designed according to the present invention. Tray portion 21 is depicted as having a generally rectangular peripheral shape and a sufficient depth to receive and store medically-related instruments, equipment, and devices. The tray portion 21 may be fabricated from plastic or metal and may alternatively be configured in different shapes and sizes. In order to attach latch 23 to the tray portion 21, a relatively flat surface on the sidewall 24 is preferred. It is also important to use latches 23 on a tray with sufficient depth so that in a "down" position, the lowermost edge of each latch bail handle 25 does not extend beyond the bottom 26 of the tray portion. As will be noted from the illustrations of FIGS. 1, 2, 2A, and 3, the pair of bail handles 25 have been lifted in the FIG. 1 illustration such that they would be suitably positioned for grasping and thereby lifting the medical case 20. In the FIGS. 2 and 2A and FIG. 3 illustrations, the bail handles have been pivoted downwardly against the sides of the tray portion as would be typical during storage or use.

The lid 22 which may be plastic or metal has a size and shape which is similar to and compatible with the upper peripheral edge 28 of the tray portion 21. In the illustrations of FIGS. 1-3, the upper peripheral edge 28 of the tray portion 21 has a radiused curvature extending upwardly and outwardly to a free edge. The lid 22 is sized to have a close-fitting relationship around and over this peripheral edge 28 so as to close off the hollow or open interior of the tray portion 21. Lid 22 has a substantially flat top surface 29, a substantially flat depending lip surface 30, and a curved bend 31 at the "corner" therebetween.

Each latch 23 includes a hook portion 34 which extends up and over the outer edge of the lid 22 and holds the lid 22 on the peripheral edge 28 in a securely retained manner. This is the closed condition for medical case 20. In order to open the medical case, the two latches are released and the lid is lifted up off of the tray portion. This action, as will be described in greater detail hereinafter, enables the hook portion 34 of each latch 23 to pivot off of the top surface 29 of lid 22 at which point the lid can be easily lifted off of the tray portion. These steps are then followed in the reverse order when it is desired to re-close the medical case.

A bail handle 25 is designed as part of each latch 23 so as to be able to pivot between a "down" position as illustrated in FIGS. 2, 2A, and 3 and an "up" position for grasping and carrying as illustrated in FIG. 1. While the size and shape of each bail handle 25 can be varied, it is important to design the handles 25 relative to the remainder of each latch 23 so that the handles pivot over an approximately 90 degree range. Another feature of the present invention is to mount the pivoting portion of each handle in s tight fitting sleeve or tube so that the bail handles 25 stay in whatever position they are placed until that position is manually changed. The preferred material for this tight fitting sleeve is silicone rubber, surgical grade. This design keeps the handles from banging against the sides of the tray portion and when pivoted up to a grasping orientation (see FIG. 1) for carrying the medical case 20, the bail handles 25 will remain in that position for quick and easy handling.

While the two latches 23 are arranged at opposite ends along the shorter sides of the tray portion, these latches could be located along the longer sides if desired. It is also envisioned that additional latches could be used or that one of the two illustrated latches could be replaced by a hinge such that with the one latch released, the lid, hingedly connected along one edge to the tray portion, pivots up away from the tray portion.

Referring to FIGS. 4, 5, 6 and 7, one latch 23 is illustrated in greater detail. In addition to bail handle 25 and latch hook 34, latch 23 includes a base 37, lever 38, two handle sleeves or tubes 39a and 39b, two connecting links 40a and 40b, two long pins 41a and 41b, and two short pins 42a and 42b. Since the assembly of these various component parts is clearly illustrated, a brief explanation should suffice. Further, the later figures depicting the major individual parts make the assembly of latch 23 clear.

Figure 10:
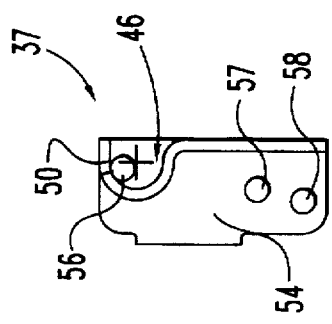
FIG. 10 is a side elevational view of the FIG. 8 base member.
Figure 8:
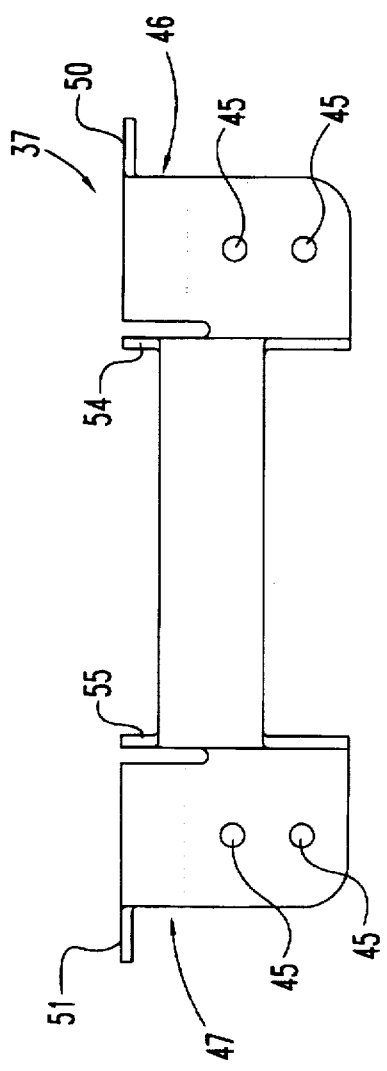
FIG. 8 is a front elevational view of a base member comprising a portion of the FIG. 4 latch.
Figure 9:
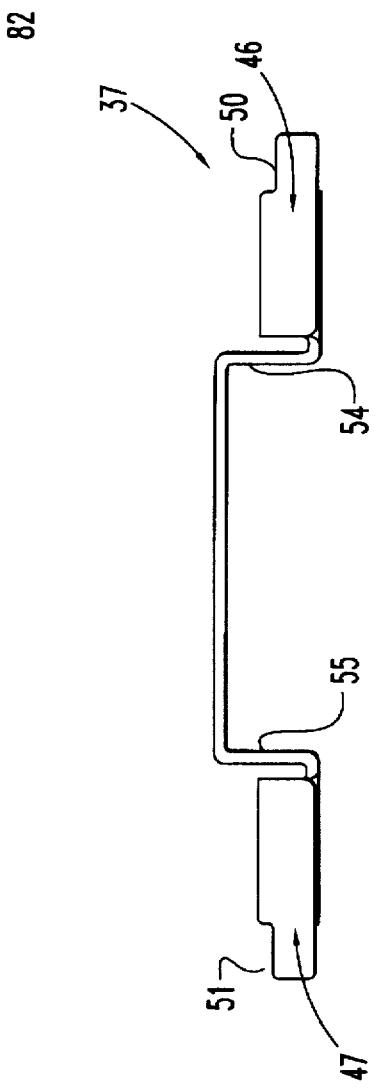
FIG. 9 is a top plan view of the FIG. 8 base member.

Base 37 (see FIGS. 8-10) is a unitary, metal component which includes a pair of rivet (or screw) holes 45 on each side for securely attaching the base directly to sidewall 24. Tube portions 46 and 47 are semi-cylindrical sleeves, each of which receive a corresponding one of the two handle tubes 39a and 39b. Each handle tube 39a and 39b is a unitary cylindrical sleeve which fits snugly within its corresponding tube portion. The preferred material for each tube 39a and 39b is silicone rubber, surgical grade. The unitary bail handle 25 is formed with two, inwardly-directed free ends 48 and 49 which fit within a corresponding one of the handle tubes. An axial line extending through the longitudinal axis of each free end defines the pivot axis for the bail handle 25. This combination is designed and constructed such that there is a tight fit, while still permitting manual pivoting movement of the bail handle as is diagrammatically illustrated in FIG. 6. The tightness of this fit is greater than the gravitational pull on the mass of the bail handle 25 such that once pivoted to a desired position, the bail handle stays in that position until manually moved to another position. A pair of oppositely-disposed upper shelves 50 and 51 control and limit the pivoting height of bail handle 25. The extent of handle travel is approximately 90 degrees.

Side panels 54 and 55 are aligned with each other and each one defines three clearance holes 56, 57 and 58. The holes in one panel are aligned with the corresponding holes in the other panel such that a straight line intersects the geometric center of hole 56 in panel 54 with the geometric center of hole 56 in panel 55. A similar aligned relationship exists for holes 57 and for holes 58. There would then accordingly be three straight imaginary lines extending from the geometric center of one hole in one panel to its corresponding hole in the other panel. These three straight imaginary lines are substantially parallel to each other and in the FIG. 4 orientation, these three lines are substantially horizontal.

Latch hook 34 (see FIGS. 11∝13) has opposite side portions 61 and 62 each of which defines two clearance holes 63 and 64 in portion 61 and holes 65 and 66 in portion 62. Holes 63 and 65 are in alignment as are holes 64 and 66 such that straight imaginary lines drawn through the geometric center of each aligned hole pair (i.e., 63 and 64/64 and 66) are substantially parallel to each other and are substantially parallel to the aforementioned three imaginary lines.

Lever 38 (see FIGS. 14–16) has opposite side panels 69 and 70 each of which defines a three-hole pattern including holes 71, 72 and 73. As should be understood, each hole in panel 69 is aligned with its corresponding hole in panel 70 such that an imaginary line extending through the geometric centers of each aligned pair is straight and substantially parallel to each of the aforementioned imaginary lines. In the FIG. 4 orientation, all of these imaginary lines are substantially horizontal.

Each link 40a and 40b (see FIG. 17) includes a pair of clearance holes 76a and 77a in link 40a and 76b and 77b in link 40b. Corresponding holes are aligned such that imaginary lines drawn through the geometric centers of holes 76a and 76b and of holes 77a and 77b are substantially parallel to each other and substantially parallel to each of the aforementioned imaginary lines.

The assembly of latch 23 involves the alignment of the base 37, lever 38, hook 34, and links 40a and 40b and the insertion of four pins 41a, 41b, 42a, and 42b into aligned clearance holes. Beginning with base 37, holes 56 are aligned with holes 63 in hook 34 and these two components are secured together in a pivoting relationship by means of long pin 41a. Holes 57 are aligned with holes 72 of lever 38 and these two components are secured together in a pivoting relationship by means of long pin 41b. Holes 58 are aligned with holes 73 of lever 38 and these holes are available for a security/tamper-evident enhancement. By threading a cable tie, wire or cable through both holes 57 and both holes 72 and securing the free ends of this cable tie into a tightly drawn and continuous loop, it is not possible to lift lever 38 without first breaking the continuous loop. There are also specific devices available for this purpose which are typically made of plastic. They have a straight shaft with a flag or tab attached to one end to indicate processing and a barbed device on the other end to allow insertion but impede removal. If lever 38 is not lifted, then the hook 34 is not released and the lid 22 stays secured onto the tray portion 21. If this tamper-evident enhancement is used, a plastic cable tie wrap with a ratcheted, self-locking hub is the preferred choice to quickly and securely attach the lever 38 to the base 37 in a closed condition. If this cable tie is severed, or not present, then the recipient (i.e., end user) of the items placed within the medical case is alerted to the fact that the items in the tray portion may have been tampered with.

Link 40a is positioned between side portion 61 of hook portion 34 and side panel 54 of base 37. Link 40b is positioned between side portion 62 and side panel 55. Holes 76a and 76b are aligned with each other and are individually aligned with holes 64 and 66. A short pin 42a is inserted through these four holes such that the free ends of pin 42 are flush with the outer surfaces of links 40a and 40b.

With continued reference to links 40a and 40b, holes 77a and 77b are aligned with each other and are individually aligned with hole 71 in panel 69 and with hole 71 in panel 70. Short pin 42b is inserted through these four holes such that the free ends of pin 42b are flush with the outer surfaces of links 40a and 40b.

In a lid-closed/latch-closed orientation, as illustrated in FIG. 6, the links 40a and 40b are oriented in a substantially vertical direction, based upon the generally horizontal orientation of latch 23 in FIG. 4. As is illustrated, the lip 80 of hook 34 is substantially horizontal and capable of hooking onto and over the upper, outer peripheral edge of lid 22. Since the lip 80 is substantially horizontal, it is capable of preventing the lid from being lifted upwardly off of the tray portion as would be required in order to separate the lid 22 from tray portion 21 in order to gain access to the tray portion 21. Broken line 81 denotes the generally vertical alignment of links 40a and 40b and at a right angle thereto is broken line 82 which denotes the horizontal plane of lip 80.

The pivot point or pivot axis for lever 38 is through the longitudinal axis of pin 41b. The location of pin 41b is to the right of broken line 81. As a consequence, the closed condition of latch 23 represents an "over-the-center" type of arrangement. When the lever 38 is pushed closed, the links 40a and 40b are pivoted from the FIG. 7 orientation to the FIG. 6 orientation. By causing the links 40a and 40b to swing past the pivot point, there is a snap-over arrangement which actually locks the latch 23 in its closed condition. Routine handling and vibrations or bumps due to transport are unable to dislodge the latch from its closed condition.

With the latch 23 in its closed condition as illustrated in FIG. 6, the release tab 83 of lever 38 extends downwardly. There is a clearance space 84 left between release tab 83 and the rear mounting surface 85 of base 37 for a finger or thumb to be inserted in order to manipulate lever 38.

When lever 38 is pulled out and pivots upwardly, and with long pin 41b serving as the pivot point, short pin 42b moves inwardly and a little downwardly. This pivots the lower end of links 40a and 40b inwardly and upwardly. This in turn pivots hook portion 34 in a counter-clockwise direction based upon the FIG. 7 orientation. The pivot point for hook 34 is defined by long pin 41a. As should be understood, the hook portion 34 pivots in a small arc without lifting up or raising the free end. This is caused by the fixed pivot point of long pin 41a which is received within side panels 54 and 55.

In order to close latch 23 and return it from the FIG. 7 opened condition to the FIG. 6 closed condition, the user merely needs to push inwardly against release tab 83. This one-finger operation to open and/or close latch 23 creates a quick and convenient latch design. The over-the-center locked position of FIG. 6 allows the latch component parts to remain stationary and flush against the sidewall of the tray portion. There are no sharp edges or corners to interfere with the desired handling and usage of the medical case 20 and the components parts of latch 23 do not move in the FIG. 6 orientation. There are no loose or dangling parts and the overall design provides a quiet and secure latch.

As has been illustrated and described, there is a single-action to latch 23 which can be completely controlled for either opening and/or closing by a single finger. The movement of the hook portion is a singular type of motion in that it scribes a smooth and continuous arc as it pivots away from lid 22 for releasing the lid and as it pivots back into a closed condition securing lid 22 onto tray portion 21. There is, as has been illustrated, a one-finger push to close and pull to open operation for latch 23. In this way, both latches 23 which are oppositely disposed at opposite ends of the medical case can be simultaneously opened and then simultaneously closed further contributing to the convenience and efficiency of the present invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A single-action latch for use on a container having a storage tray and a closing lid, said latch comprising:

a latch base having a mounting surface and means for attaching said latch base to the storage tray;

a hook portion pivotally attached to said latch base;

a release/closing lever pivotally attached to said latch base;

a pair of oppositely-disposed connecting links wherein each connecting link being pivotally connected at one end to said hook portion and being pivotally connected at an opposite end to said lever; and said latch being operable between a closed condition wherein said hook portion secures said closing lid to said storage tray and an opened condition wherein said closing lid is separable from said storage tray, said lever being pivotally movable so as to transition said latch from said closed condition to said opened condition and back to said closed condition.

2. The single-action latch of claim 1 wherein said release/closing lever has a pivot axis and said pair of oppositely-disposed connecting links are spaced apart from said axis so as to provide an over-the-center arrangement.

3. The single-action latch of claim 2 wherein said hook portion is pivotally attached to said latch base by means of a substantially cylindrical pin.

4. The single-action latch of claim 3 wherein said release/closing lever is pivotally attached to said latch base by means of a substantially cylindrical pin.

5. The single-action latch of claim 4 wherein said pair of oppositely-disposed connecting links are connected to said hook portion by a first pin and to said lever by a second pin.

6. The single-action latch of claim 5 which further includes a bail handle pivotally mounted to said latch base.

7. The single-action latch of claim 6 wherein said bail handle has two free ends which are mounted into corresponding semi-cylindrical sleeves, said sleeves being received by oppositely disposed portions of said latch base.

8. The single-action latch of claim 1 which further includes a bail handle pivotally mounted to said latch base.

9. The single-action latch of claim 8 wherein said bail handle has two free ends which are mounted into corresponding semi-cylindrical sleeves, said sleeves being received by oppositely disposed portions of said latch base.

10. A medical case for the storage of medically-related instruments and equipment, said medical case comprising:

a tray portion having an open top, base and surrounding sidewalls;

a lid sized and constructed to fit over said tray portion and close said open top; and a pair of single-action latches, each latch being securely attached to a sidewall of said tray portion along opposite sides of said tray portion, each latch comprising:
    (a) a latch base having a mounting surface and means for attaching said latch base to the storage tray;
    (b) a hook portion pivotally attached to said latch base;
    (c) a release/closing lever pivotally attached to said latch base;
    (d) a pair of oppositely-disposed connecting links wherein each connecting link being pivotally connected at one end to said hook portion and being pivotally connected at an opposite end to said lever; and
    (e) said latch being operable between a closed condition wherein said hook portion secures said closing lid to said storage tray and an opened condition wherein said closing lid is separable from said storage tray, said lever being pivotally movable so as to transition said latch from said closed condition to said opened condition and back to said closed condition.

11. The medical case of claim 10 wherein each release/closing lever has a pivot axis and each pair of oppositely-disposed connecting links are spaced apart from said axis so as to provide an over-the-center arrangement.

12. The medical case of claim 11 wherein each hook portion is pivotally attached to its corresponding latch base by means of a substantially cylindrical pin.

13. The medical case of claim 12 wherein each release/closing lever is pivotally attached to its corresponding latch base by means of a substantially cylindrical pin.

14. The medical case of claim 13 wherein each pair of oppositely-disposed connecting links are connected to said corresponding hook portion by a first pin and to said corresponding lever by a second pin.

15. The medical case of claim 14 wherein each latch further includes a bail handle pivotally mounted to the corresponding latch base.

16. The medical case of claim 15 wherein each bail handle has two free ends which are mounted into corresponding semi-cylindrical sleeves, said sleeves being received by oppositely-disposed portions of a corresponding latch base.

17. A single-action latch for use on a container having a storage tray and a closing lid, said latch comprising:

a latch base having a mounting surface and means for attaching said latch base to the storage tray;

a hook portion pivotally attached to said latch base;

a release/closing lever pivotally attached to said latch base;

a pair of oppositely-disposed connecting links wherein each connecting link being connected at one end to said hook portion and at an opposite end to said lever; and said latch being operable between a closed condition wherein said hook portion secures said closing lid to said storage tray and an opened condition wherein said closing lid is separable from said storage tray, said lever being pivotally movable so as to transition said latch from said closed condition to said opened condition and back to said closed condition.

* * * * *

UNITED STATES PATENT AND TRADEMARK OFFICE
CERTIFICATE OF CORRECTION

PATENT NO. : 5,630,507
DATED : May 20, 1997
INVENTOR(S) : Terry L. Baker

It is certified that error appears in the above-indentified patent and that said Letters Patent is hereby corrected as shown below:

In Col. 2, at line 37, replace "tile" with --the--.

In Col. 4, at line 4, replace "tile" with --the--.

In Col. 4, at line 13, replace "tile" with --the--.

In Col 4, at line 13 after the word "in", replace "s" with --a--.

In Col. 5, at line 9, replace "11∝13" with --11-13--.

Signed and Sealed this

Thirtieth Day of September, 1997

Attest:

BRUCE LEHMAN

Attesting Officer

Commissioner of Patents and Trademarks